United States Patent [19]

Barton et al.

[11] 4,256,661
[45] Mar. 17, 1981

[54] PRODUCTION OF THIOSEMICARBAZIDE

[75] Inventors: Danny B. Barton, Kansas City; Chester W. Halbleib, Holt; Jack J. Lonsinger, Liberty, all of Mo.

[73] Assignee: Mobay Chemical Corporation, N.J.

[21] Appl. No.: 90,213

[22] Filed: Nov. 1, 1979

Related U.S. Application Data

[63] Continuation of Ser. No. 904,345, May 9, 1978, abandoned.

[51] Int. Cl.$^3$ .................................... C07C 159/00
[52] U.S. Cl. ............................................. 564/18
[58] Field of Search .................................. 260/552 SC

[56] References Cited

U.S. PATENT DOCUMENTS

| | | |
|---|---|---|
| 2,710,243 | 6/1955 | Swimmer ............... 260/552 SC X |
| 2,771,489 | 11/1956 | Audrieth et al. ............ 260/552 SC |
| 3,009,955 | 11/1961 | Rieche et al. ............... 260/552 SC |
| 3,067,250 | 12/1962 | Oja ............................ 260/552 SC |
| 3,318,772 | 5/1967 | Berger et al. ............ 260/552 SC X |

Primary Examiner—Thomas A. Waltz
Attorney, Agent, or Firm—Sprung, Felfe, Horn, Lynch & Kramer

[57] ABSTRACT

In the production of thiosemicarbazide comprising the steps of reacting hydrazine and ammonium thiocyanate to form hydrazinium thiocyanate and by-product ammonia, and heating the hydrazinium thiocyanate to effect isomerization thereof to thiosemicarbazide, the improvement which comprises removing the ammonia from the hydrazinium thiocyanate prior to isomerization thereof, whereby the thiosemicarbazide is produced in high yield and purity. Advantageously at least about 80% of the ammonia is removed by steam stripping and/or vacuum distillation and the subsequent isomerization is effected by prolonged heating in the presence of a carbonyl compound such as acetone or acetaldehyde. The thiosemicarbazide is recovered by cooling to effect crystallization, followed by filtration, the mother liquor being recycled as solvent medium for the next batch.

4 Claims, No Drawings

PRODUCTION OF THIOSEMICARBAZIDE

This is a continuation, of application Ser. No. 904,345, filed May 9, 1978, now abandoned.

The present invention relates to the production of thiosemicarbazide by the isomerization of hydrazinium thiocyanate.

Thiosemicarbazide and its derivatives are widely used as intermediates in the manufacture of pharmaceuticals, pesticides, polymer stabilizers, and the like, undergoing condensations to form heterocyclic rings, substitutions to replace hydrogen atoms, etc.

German DAS No. 1,274,574 discloses several earlier processes for preparation of thiosemicarbazide and then sets forth its own improvement thereover, involving reacting ammonium thiocyanate with dihydrazine sulfate in water, apparently forming hydrazinium thiocyanate and ammonium sulfate. Heating of the solution in the presence of acetaldehyde effects isomerization and cooling serves to precipitate thiosemicarbazide. While this process is satisfactory, it also produces by-product ammonium sulfate and accordingly there is a recovery and/or disposal problem. In addition, the yields are not as high as might be desired for maximum efficiency.

British Pat. No. 1,118,133 discloses refluxing a mixture of hydrazine, ammonium thiocyanate and n-butanol with acetone as a catalyst to produce thiosemicarbazide. Obviously an organic solvent is required, which presents problems of cost and safety.

It is accordingly an object of the present invention to provide an inexpensive, safe overall process for going from ammonium thiocyanate to thiosemicarbazide in high conversion and high yield.

These and other objects are realized in accordance with the present invention pursuant to which hydrazine is reacted with ammonium thiocyanate to form hydrazinium thiocyanate and ammonia, and the hydrazinium thiocyanate is isomerized to thiosemicarbazide. The present invention requires measures to be taken to remove most of the ammonia prior to the isomerization, thereby increasing the yield of thiosemicarbazide. The process thus involves the following reactions:

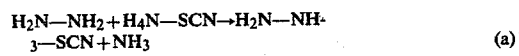

(a)

(b)

Reaction (a) is advantageously effected in water although organic solvents can be added. The amount of water can be just enough to keep the masses soluble under the reaction conditions but not so much as will dissolve too much thiosemicarbazide and thus complicate recovery in step (b). Water charged for preparation of hydrazinium thiocyanate can be an amount required to form a 10 to 80% by wt. solution of equivalent hydrazinium thiocyanate but preferably the amount required to form a 25 to 65% solution.

The ammonium thiocyanate and hydrazine are preferably charged in approximately equimolar proportions, although a slight excess of ammonium thiocyanate, e.g. about 20% and preferably no more than about 10%, may be desirable to ensure the complete utilization of the hydrazine which is relatively costly. If the process is conducted in batches with re-cycle, discussed more fully hereinbelow, excess ammonium thiocyanate may be used in the first cycle and substantially equimolar amounts in subsequent cycles.

The hydrazine may be added in pure form, in the form of its hydrate, or as an aqueous solution, and the amount of water introduced therewith will be taken into consideration in carrying out the process.

Reaction (a) is substantially completed by removal of ammonia according to methods discussed in the present invention. Removal of ammonia can be effected by simple batch distillation at atmospheric pressure, at reduced pressures, or by use of an inert gas strip in conjunction with or in the place of reduced pressures. The temperature range during this operation for suitable ammonia removal is about 25° C. to 110° C. The most suitable method for ammonia removal, however, is by steam stripping or multistage distillation, i.e. by introducing the solution near the top plate of a distillation column and either injecting steam into the bottom of the column or vaporizing water from solution up the column and counter-current to the feed. The vapors from the top of the column consist of water, ammonia, and traces of impurities which condense to form a solution of ammonium hydroxide easily made suitable for synthesizing additional ammonium thiocyanate. From the bottom of the column a solution is recovered which is ready for isomerization.

Such process may be carried out under atmospheric pressure or even under vacuum or slight positive pressure. The temperature is not important although elevated temperatures, e.g. about 60° to above 100° C., will speed up the ammonia removal. Advantageously, at least about 80% and preferably at least about 95% of the available ammonia formed in reaction as determined by stoichiometry (a) is so removed.

Thereafter, step (b) is effected preferentially, but not exclusively, by catalysis, e.g. a carbonyl-containing catalyst is added, the mass is heated to effect isomerization, it is cooled to precipitate thiosemicarbazide, and it is filtered to recover the thiosemicarbazide.

As carbonyl-containing catalyst, acetone and acetaldehyde have proven especially effective although other carbonyl compounds are also effective, e.g., methylisobutylketone, benzaldehyde, and the like. The catalyst can be employed in about 0.01 to 0.2 and preferably about 0.05 to 0.08 mole per mole of hydrazinium thiocyanate undergoing isomerization.

The isomerization can reasonably be effected at about 80° to 130° C. but temperatures near 105° C. are preferred since they can be maintained by simply boiling with reflux, at atmospheric pressure. The isomerization is not pressure-dependent so vacuum or positive pressures can also be utilized. The extent of isomerization is generally time dependent but, if conducted batchwise, at atmospheric reflux, about 2 hours is suitable for practical purposes. Usually isomerization is carried out to the extent of about 35 to 60% completion, preferably about 50%, with the mother liquor ultimately obtained and containing un-isomerized material being recycled for further use. The isomerized product precipitates out and, at conversions higher than recited, the insoluble product becomes too thick in the slurry to handle and would require additional water for dilution. This is undesirable since there is normally water build-up and because if the filtrate (containing the precursor) is to be recycled the water should be kept to a minimum. In a continuous process where the product is filtered off and the filtrate recycled, there is nothing lost of the precursor in the filtrate which is subsequently recycled to the isomerization step.

Of course one could carry the isomerization to completion, meaning little or no precursor is left, but the yield and purity would decrease and a dilution with water would be required for ease of handling the thick slurry. Thus, it would be possible to operate practically with as little as about 5–10% isomerization, removal of the product formed and recycle of the mother liquor.

Thereafter the mass is cooled, advantageously below about 50° C. and preferably below about 25° C., whereupon thiosemicarbazide crystallizes out. Simple filtration followed by washing the crude cake with water results in product of suitable purity for use in chemical synthesis.

In accordance with a preferred aspect of the present invention the mother liquor is used for another batch in place of water in effecting step (a). Since there would be water build-up, this is dealt with by recycling only part of the mother liquor, by concentration of the mother liquor before recycling, and/or by removal of some water during the ammonia strip or isomerization.

The invention will be further described in the following illustrative examples:

EXAMPLE 1

251 g ammonium thiocyanate (3.3 moles) is dissolved in 140 5 g hydrazine hydrate (2.81 moles) and 45.5 g $H_2O$. The resulting solution is passed counter-current to 448 g of atmospheric steam in a distillation column, 581 g of a 43.1% by weight solution of hydrazinium thiocyanate being withdrawn as still bottoms at 108° C. The distillate is cooled to 25° C. in a condenser, yielding 351 g of a 13.3% by weight solution of ammonia in water, corresponding to 2.75 moles of ammonia. 68 g water is charged to the 581 g hydrazinium thiocyanate solution to adjust the hydrazinium thiocyanate concentration to 38.6%. 9.0 g of acetone are added to the hydrazinium thiocyanate solution and the solution is heated for 2 hours at atmospheric pressure with reflux, a portion of the hydrazinium thiocyanate isomerizing to thiosemicarbazide. The solution is cooled to 20° C., precipitating thiosemicarbazide which is recovered by filtration, 124 g of m.p. 178°–9° C. being recovered after washing the cake with water and drying. The 489 g filtrate containing unconverted hydrazinium thiocyanate is concentrated to 229 g and used in place of the 45.5 g of water for dissolving fresh ammonium thiocyanate in another batch. Over 3 additional cycles the thiosemicarbazide yield (hydrazine hydrate basis) is 96.3% (includes recycle of cake wash water with filtrate).

EXAMPLE 2

In order to accomplish sufficient conversion of ammonium thiocyanate to hydrazinium thiocyanate by vacuum distillation for isomerization. The following procedure is recommended: Charge 152 g ammonium thiocyanate (2.0 moles) to an agitated flask and dissolve this in 350 g $H_2O$ and 103 g hydrazine hydrate (2.06 moles) maintaining the solution temperature at 50° C., remove water and ammonia by simple distillation from an initial 105 mmHg to a final 10 mmHg absolute pressure and a final bottoms weight of 200 g. To the viscous residue in the agitated flask charge 350 g $H_2O$ and blend. Maintaining the solution temperature at 55° C., remove water and residual ammonia by simple distillation at 20 to 8 mmHg absolute pressure. To the final 187 g of viscous bottoms product is charged 100 g water. By analysis, these bottoms contain 62.0% hydrazinium thiocyanate and 3.9% ammonium thiocyanate for an effective 92.6% removal of available ammonia. 1.85 moles of ammonia is removed by the distillation and collected as a solution with water as condensate.

EXAMPLE 3

In order to exemplify the catalytic conversion of hydrazinium thiocyanate to thiosemicarbazide using acetaldehyde as a catalyst, the following procedure is outlined: 228 g ammonium thiocyanate (3.0 mol) is dissolved in 140.6 g hydrazine hydrate (2.812 mol) and 45.4 g water. This solution is fed into the top of a distillation column while 1050 g steam is passed counter-current to the feed in an upward direction through the distillation column. 46.6 g ammonia (2.74 moles) is removed in the steam and recovered as an ammonia and water solution by condensation. 637 g of the hydrazinium thiocyanate solution is recovered from the bottom of the column. To this solution is charged 9.0 g acetaldehyde (0.205 moles) catalyst, the total being then heated at atmospheric reflux for 2 hours. After cooling to 20° C., the thiosemicarbazide formed is recovered from solution by filtration and washed with 200 g water. The final, dry thiosemicarbazide cake weight is 123.5 g which represents a 93.5% yield of thiosemicarbazide from the total hydrazinium thiocyanate removed from the solution during cooking.

It will be appreciated that the instant specification and examples are set forth by way of illustration and not limitation, and that various modifications and changes may be made without departing from the spirit and scope of the present invention.

What we claim is:

1. In the production of thiosemicarbazide comprising the steps of reacting hydrazine and ammonium thiocyanate in aqueous solution to form hydrazinium thiocyanate and by-product ammonia, and heating the solution to effect isomerization of the hydrazinium thiocyanate to thiosemicarbazide, the improvement which comprises removing at least about 80% of the stoichiometric amount of the ammonia from the solution at a temperature from about 25° to 110° C., heating the solution up to about 105° C. to effect isomerization of about 35 to 60% of the stoichiometric amount of the hydrazinium thiocyanate, cooling whereby the thiosemicarbazide is selectively precipitated in high yield and purity, and recycling the residual solution as the solvent medium for further reaction of hydrazine and ammonium thiocyanate.

2. The process according to claim 1, wherein the ammonia is removed from the solution in which it is formed by steam stripping.

3. The process according to claim 1, wherein the ammonia is removed from the solution in which it is formed by vacuum distillation.

4. The process according to claim 1, wherein the molar ratio of hydrazine to ammonium thiocyanate is from about 0.7 to 1.2:1.

* * * * *